United States Patent
Honda

(10) Patent No.: US 8,774,478 B2
(45) Date of Patent: Jul. 8, 2014

(54) MEDICAL IMAGE PROCESSING DEVICE AND METHOD FOR RECORDING INCIDENTAL INFORMATION

(75) Inventor: Masashi Honda, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 722 days.

(21) Appl. No.: 12/121,338

(22) Filed: May 15, 2008

(65) Prior Publication Data

US 2008/0285832 A1 Nov. 20, 2008

(30) Foreign Application Priority Data

May 16, 2007 (JP) ................... 2007-130551

(51) Int. Cl.
*G06K 9/00* (2006.01)
(52) U.S. Cl.
USPC .......................................... 382/131; 600/440
(58) Field of Classification Search
CPC ........ A61B 6/463; A61B 6/465; G06F 19/30; G06T 7/0012
USPC ................... 382/128, 131; 600/440
See application file for complete search history.

(56) References Cited

U.S. PATENT DOCUMENTS

| | | | |
|---|---|---|---|
| 6,464,638 B1 * | 10/2002 | Adams et al. ................. | 600/443 |
| 7,103,205 B2 * | 9/2006 | Wang et al. ................... | 382/132 |
| 7,391,423 B1 * | 6/2008 | Manzari et al. ............... | 345/619 |
| 7,615,008 B2 * | 11/2009 | Zhang et al. .................. | 600/437 |
| 7,783,094 B2 * | 8/2010 | Collins et al. ................ | 382/128 |
| 7,920,152 B2 * | 4/2011 | Fram et al. .................... | 345/661 |
| 2006/0257009 A1 * | 11/2006 | Wang et al. .................... | 382/128 |
| 2008/0117225 A1 * | 5/2008 | Wegenkittl et al. ........... | 345/581 |

FOREIGN PATENT DOCUMENTS

| | | |
|---|---|---|
| JP | 3-49742 | 3/1991 |
| JP | 3-293393 | 12/1991 |
| JP | 4-212336 | 8/1992 |
| JP | 5-324785 | 12/1993 |
| JP | 6-327623 | 11/1994 |
| JP | 6-339467 | 12/1994 |
| JP | 7-37061 | 2/1995 |
| JP | 7-129754 | 5/1995 |
| JP | 7-282229 | 10/1995 |
| JP | 10-137190 | 5/1998 |
| JP | 10-323328 | 12/1998 |
| JP | 2000-300538 | 10/2000 |
| JP | 2001-5902 | 1/2001 |
| JP | 2002-32068 | 1/2002 |

(Continued)

OTHER PUBLICATIONS

Japanese Office Action issued May 15, 2012 in Patent Application No. 2007-130551.

(Continued)

*Primary Examiner* — Shefali Goradia

(74) *Attorney, Agent, or Firm* — Oblon, Spivak, McClelland, Maier & Neustadt, L.L.P.

(57) ABSTRACT

An ultrasonic apparatus images incidental information including at least either subject information or examination information to generate an incidental information image, and executes information processing of the incidental information image as an independent frame from a series of ultrasonic images as well as information processing to form the incidental information image as a series of images with the ultrasonic images.

7 Claims, 8 Drawing Sheets

(56) References Cited

FOREIGN PATENT DOCUMENTS

| | | |
|---|---|---|
| JP | 2005-34498 | 2/2005 |
| JP | 2005-279097 | 10/2005 |
| JP | 2005-312774 | 11/2005 |
| JP | 2005-334634 | 12/2005 |
| WO | WO 03/001421 A1 | 1/2003 |

OTHER PUBLICATIONS

Office Action dated Nov. 19, 2013, in Japanese Patent Application No. 2013-016016 (in Japanese language).

* cited by examiner

FIG. 1

Examination List

| Patient ID | Name | Date |
|---|---|---|
| 12345670 | ***************** | ******************* |
| 12345671 | ***************** | ******************* |
| 12345672 | ***************** | ******************* |
| 12345673 | ***************** | ******************* |
| 12345674 | ***************** | ******************* |
| 12345675 | ***************** | ******************* |
| 12345676 | ***************** | ******************* |
| 12345677 | ***************** | ******************* |
| 12345678 | ***************** | ******************* |
| 12345679 | ***************** | ******************* |
| 12345680 | ***************** | ******************* |
| 12345681 | ***************** | ******************* |
| 12345682 | ***************** | ******************* |
| 12345683 | ***************** | ******************* |
| 12345684 | ***************** | ******************* |
| 12345685 | ***************** | ******************* |

MEDICAL IMAGE PROCESSING DEVICE AND METHOD FOR RECORDING INCIDENTAL INFORMATION

BACKGROUND OF THE INVENTION

1. Field of the Invention

The present invention relates to technology for processing incidental information related to medical images.

2. Description of the Related Art

A medical image processing device is a device for generating an image from information of a tissue within a subject body, such as a fluoroscopic image, a tomographic image and a blood flow image within the subject body, thereby conducting an examination and a diagnosis. As the medical image processing device, there are various modalities for medical image processing. Examples include an X-ray diagnostic apparatus, an X-ray CT (Computed Tomography: X-ray computer tomography) device, an MRI (Magnetic Resonance Imaging) device, ultrasonic diagnostic equipment, and an NM (Nuclear Medicine).

An examiner conducts an examination with the medical image processing device. Tissue information within a subject body is collected in the examination. Moreover, the tissue information is imaged by the medical image processing device as a moving image or still image, whereby a medical image is generated. By viewing the medical image in real time, or reproducing and viewing the medical image having been stored, an examination and diagnosis of a disease is conducted, for example. Moreover, the examiner views the image and creates an examination report.

A conventional medical image processing device displays information such as a patient ID, patient name and examination date, in a viewer of an examination list screen as shown in FIG. 1 for a person viewing a medical image. When the viewing person selects one of the examinations from the examination list screen, an ultrasonic image as shown in FIG. 2 is displayed. The viewing person conducts a diagnosis or the like based on the ultrasonic image as shown in FIG. 2. FIG. 1 is a schematic view of an examination list in which stored medical images are listed and displayed for each examination. FIG. 2 is a schematic view of an ultrasonic image showing an example of a medical image.

As shown in FIG. 2, information on the inside of a subject is displayed substantially in the center of the screen of the viewer. The viewing person views an inside image 400 as shown on this screen, and conducts a diagnosis or the like based on the information. The viewing person needs to conduct the diagnosis or the like, by referring to not only the inside image 400 but also incidental information or the like that is not displayed in the inside image 400. The incidental information includes detailed information on the subject such as the height and weight thereof and previously reported comments on the health condition thereof, and information related to examinations.

Further, before starting to acquire information on the inside of a subject by using the medical image processing device, an examiner generally checks the height and weight of the subject and the comments on the subject. The examiner conducts an examination of the subject after the check.

In the conventional medical image processing device, the incidental information is displayed in a restricted region on the screen, such as an incidental information display column 401 above the inside image shown in FIG. 2. That is, the incidental information is displayed together with the inside image of the subject, and therefore, a space for displaying the incidental information is restricted. As a result, only supplementary information is displayed as the incidental information. The supplementary includes only identification information of the subject such as patient ID, patient name, examination date, gender and hospital name, and some information on the patient.

Further, in the examination list shown in FIG. 1, a display space is restricted for the convenience of display of the list, as in the incidental information display column. Therefore, it is impossible to display much information in the examination list. As a result, only part of the information for specifying the examination, such as patient ID, patient name and examination date, is displayed.

Further, there is a case where DICOM (Digital Imaging and Communications in Medicine) is used as a network standard of a medical image management system. In this case, a medical image is managed as a DICOM image. Moreover, in this case, identification information of a patient, which is displayed together with the inside image or displayed in the examination list, is added to the medical image as tag information (DICOM tag) according to the standard.

Furthermore, there is such a conventional ultrasonic diagnostic apparatus that records a moving image as a medical image on a VCR tape. Regarding this ultrasonic diagnostic apparatus, technology for enabling check of the identification information even when fast-forwarding or rewinding the recorded moving image has been proposed (e.g., Japanese Unexamined Patent Application Publication No. JP-A 3-49742). That is, by conducting an examination while operating a switching button (a call key), the examiner can record display screen data of the identification information. Consequently, even when the moving image is displayed at a high speed as in fast-forwarding or rewinding, the examiner can check the presence of the display screen of the identification information.

The viewing person may wish to check incidental information (patient information) of a subject having been acquired previously, the name of a doctor requesting an examination, disease information, etc., other than the inside image of the subject and the identification information of the subject as shown in FIG. 2. The incidental information of a subject includes, for example, the height/weight of the subject, comments on the health condition, etc. In this aspect, for the ultrasonic diagnostic apparatus described above, the viewing person needs to perform complicated operations in order to refer to the patient information, etc. For example, the viewing person needs to analyze data, or prepare other information as a reference. Such a problem exists in not only the ultrasonic diagnostic apparatus disclosed in JP-A 3-49742 but also conventional medical image processing devices.

Further, if there is no compatibility in standard, or if there is no incidental information display function compatible with standard, there is case where the viewing person cannot view identification information when viewing a medical image recorded in a medical image processing device. That is, there is a case where the standard of the viewer (image display device, terminal, etc.) is not compatible with the network standard of the medical image management system related to the medical image processing device. In this case, even if the identification information is attached to the medical image by the medical image processing device as the tag information, the viewer may be unable to recognize and display the identification information due to the problem on the standard.

Further, in a case where detailed information related to a subject or an examination is displayed in the examination list as shown in FIG. 1 for searching a recorded medical image, a space for display becomes insufficient. Therefore, the detailed information cannot fit in the examination list screen when included in the examination list. That is, in a case where the detailed information is included in the examination list, the viewing person cannot view the detailed information unless performing an operation such as sliding on the examination list screen, which is complicated.

Further, in the ultrasonic diagnostic apparatus as described above, when a person viewing a medical image attempts to view detailed information on a subject or examination, the viewing person needs to perform an operation of switching screens while operating a switching button (a call key). However, this operation is complicated, and may cause trouble to operations of the person viewing the medical image and the examiner. Furthermore, if an examination work using the medical image processing device is complicated, it is difficult to perform the operation of switching screens. As a result, in JP-A 3-49742, it is difficult to record display screen data of identification information such as patient ID. In this case, it is impossible to record necessary information, which may cause trouble to a diagnosis work or the like of the person viewing the medical image.

SUMMARY OF THE INVENTION

The present invention was made in consideration of the aforementioned problems, and an object of the present invention is to provide technology that makes it possible to check necessary information in detail and with ease when viewing a medical image, without adding any special function to a medical image display device and without requiring any extra operation when viewing a recorded medical image. Another object of the present invention is to provide technology that makes it possible to check necessary incidental information when viewing a medical image, even if there is a difference in medical image management standard regarding how to handle incidental information.

For the purpose of solving the above problems, in a first aspect of the present invention, a medical image processing device comprises: an image generator configured to generate an inside image based on inside information showing a tissue within a subject acquired in an examination of the subject and, upon receiving incidental information including at least either information on the subject or information on the examination, generate an incidental information image based on the incidental information; and an information processor configured to form the incidental information image in an independent frame from the inside image, execute information processing of the incidental information image as a series of images with the inside image, and output the image.

Further, in a second aspect of the present invention, a recording method in a medical image processing device configured to generate an inside image based on inside information showing a tissue within a subject acquired in an examination of the subject, for recording incidental information related to the examination, comprises: acquisition of the incidental information related to the examination; generation of an incidental information image based on the incidental information upon receiving the incidental information including at least either information on the subject or information on the examination; collection of the inside information; image generation to generate the inside image based on the inside information; and information processing to form the incidental information image in an independent frame from the inside image, execute image processing of the incidental information image as a series of images with the inside image, and output the image.

EFFECTS OF THE INVENTION

The medical image processing device according to the present invention forms the incidental information image including at least one of the information on the subject and the information on the examination in a frame independent of that for the inside image. Furthermore, it is configured to output after performing image processing on the incidental information image as a series of images with the inside image. Therefore, it is possible to reduce workload and increase efficiency in diagnosis.

BRIEF DESCRIPTION OF THE DRAWINGS

FIG. 1 is a schematic view of an examination list in which recorded medical images are listed and displayed for each examination.

DETAILED DESCRIPTION OF THE EMBODIMENTS

As an embodiment of the present invention, application of the present invention to an ultrasonic diagnostic apparatus will be described below referring to FIGS. 1 to 8.

FIRST EMBODIMENT

Entire Configuration

Figure 2:
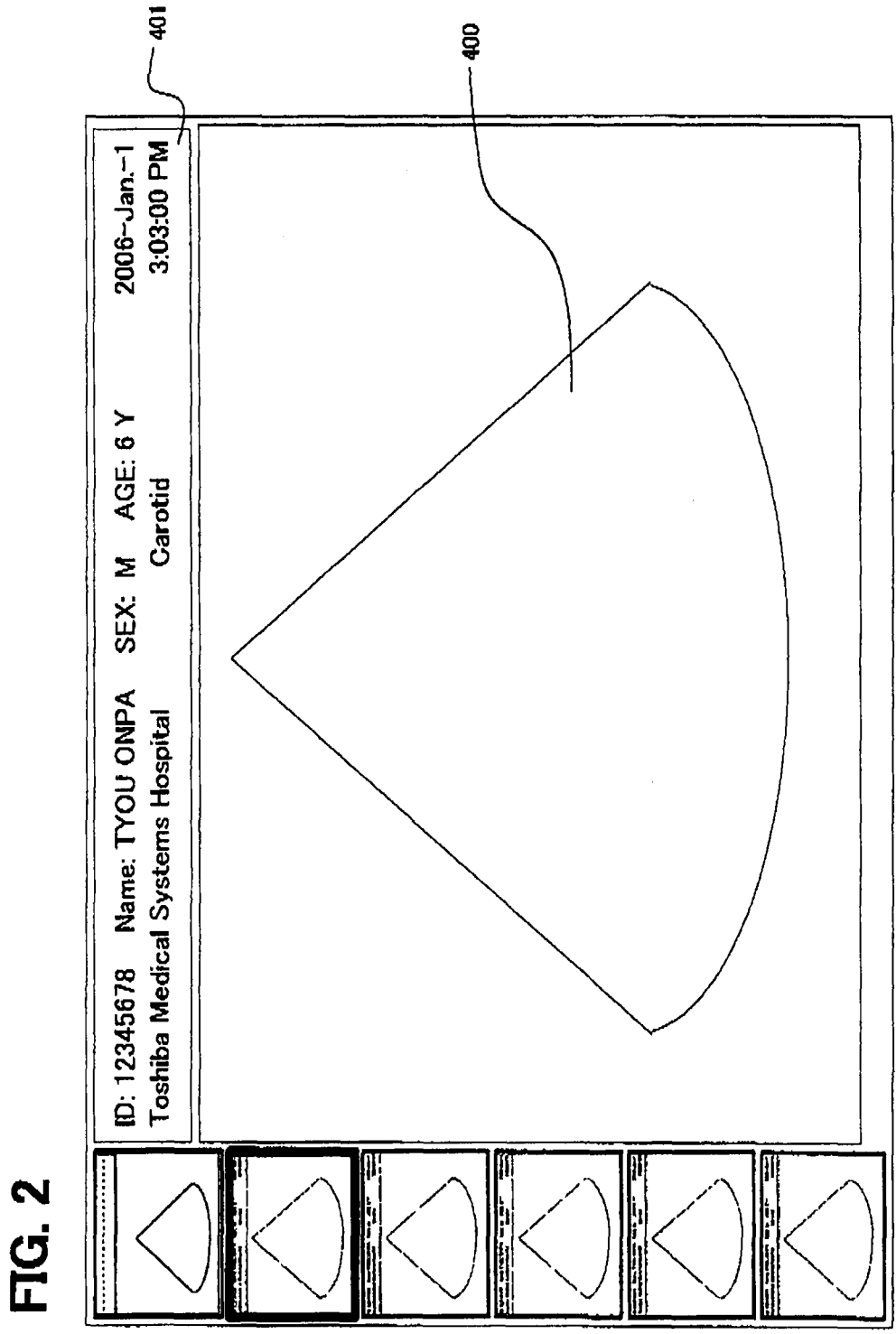
FIG. 2 is a schematic view of an ultrasonic image showing an example of a conventional medical image.
Figure 3:
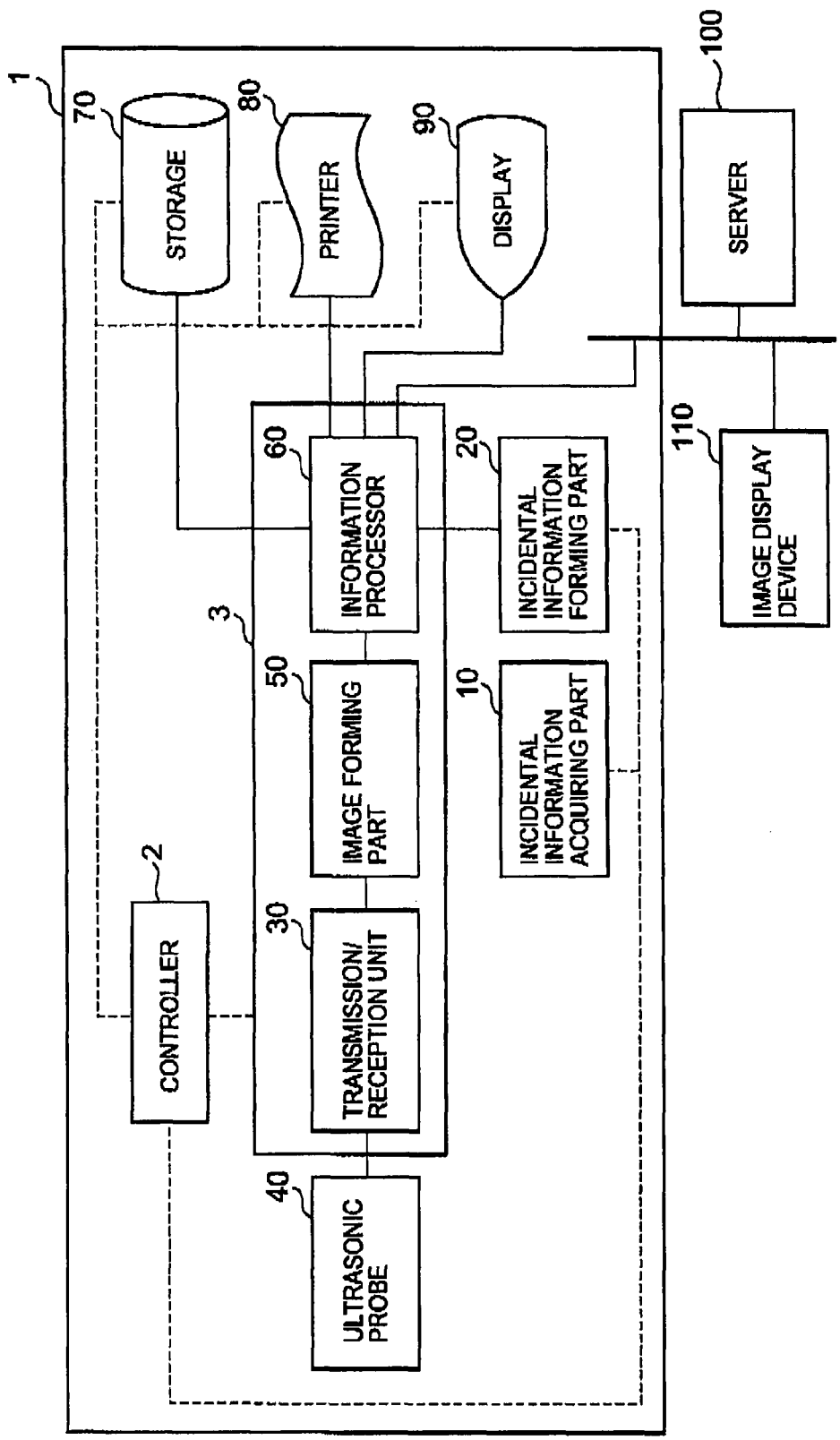
FIG. 3 is a block diagram showing a schematic configuration of an ultrasonic diagnostic apparatus in an embodiment of the present invention.

The configuration of the ultrasonic diagnostic apparatus in a first embodiment of the present invention will be described referring to FIG. 3. FIG. 3 is a block diagram showing a schematic configuration of an ultrasonic diagnostic apparatus 1 in the embodiment of the present invention.

The ultrasonic apparatus 1 in this embodiment acquires identification information and patient/examination information acquired by an incidental information acquiring part 10. Moreover, the ultrasonic apparatus 1 generates incidental information image data in an incidental information forming part 20 based on the acquired identification information and patient/examination information, accompanied by the acquisition of inside information of a subject. Moreover, the ultrasonic apparatus 1 acquires the inside information of the subject via a transmission/reception unit 30 and an ultrasonic probe 40. The ultrasonic apparatus 1 generates a series of ultrasonic image data by an image forming part 50 based on the acquired inside information of the subject. An information processor 60 of the ultrasonic apparatus 1 executes processing on the incidental information image data and ultrasonic image data having been thus acquired. As a result of the processing by the ultrasonic apparatus 1, an incidental information image is formed in a frame independent of that for the series of ultrasonic images (corresponds to an example of the "inside images" in the present invention), and is formed as a series of images with the ultrasonic images (an ultrasonic image display screen 300 in FIG. 5). The information processor 60 outputs the processed data to a storage 70, a printer 80 or a display 90 in the ultrasonic apparatus 1, or outputs the same to an external server 100. An operation of each part is controlled by a controller 2. The configuration of each part of the ultrasonic apparatus 1 will now be described.

(Configuration of Incidental Information Acquiring Part)

Next, the configuration of the incidental information acquiring part 10 will be described.

The incidental information acquiring part 10 receives order information of an examination from an HIS (Hospital Information System) or an RIS (Radiology Information System). The HIS executes reception of patients, reception for an attending department, management of individual information of patients, and accounting process of diagnosis and treatment expenses. The RIS conducts reservation of diagnosis and treatment using medical equipment such as a medical image processing device in the radiology department, reception of an examination, storage of examination data, and so on. The order information of an examination is information on a request for an examination for each subject by using the ultrasonic apparatus 1. Moreover, the incidental information acquiring part 10 may acquire information inputted by an examiner in the ultrasonic apparatus 1, or may acquire information such as an electronic medical record having been previously stored in the storage 70. Thus, the incidental information acquiring part 10 collects patient information and examination information.

Prior to an examination, the ultrasonic apparatus 1 receives an order of the examination conducted by the ultrasonic apparatus 1 from the HIS or the RIS. The order information of the examination includes identification information of a subject, such as patient ID, patient name, examination date, gender, and hospital name. The incidental information acquiring part 10 acquires the information included in the order information. Furthermore, in the ultrasonic apparatus 1, information such as an examined site, the name of a doctor requesting the examination, a hospital name and the name of a diagnosis and treatment department and examination information on the examination are previously stored for each ordered examination. The incidental information acquiring part 10 acquires the stored information. In some medical institutions, an examination order is made without using an information system such as the HIS and the RIS. In this case, incidental information such as identification information and examination information is inputted by an examiner using an operation part (not illustrated) of the ultrasonic apparatus 1, and stored in the ultrasonic apparatus 1.

Further, the storage 70 stores patient information acquired previously, such as the height/weight, age, history of hospital visits, treatment status, blood pressure, diseases and smoking habits of a subject to be examined, and comments or opinions of a doctor regarding the patient's health condition. The incidental information acquiring part 10 acquires the patient information. The patient information may be stored in the storage 70 after inputted by the examiner or others, or may be transmitted from the HIS or the like to the ultrasonic apparatus 1 in conjunction with reception of the examination order (or start of the examination) by the ultrasonic apparatus 1. Moreover, the patient information may be attached to the order information of the examination.

Furthermore, the incidental information acquiring part 10 classifies the incidental information acquired per item, and sequentially transmits the classified incidental information to the incidental information forming part 20.

(Configuration of Incidental Information Forming Part)

Figure 4:
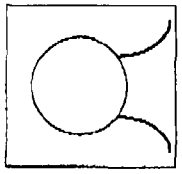
FIG. 4 is a schematic view showing an incidental information display screen in the ultrasonic diagnostic apparatus in the embodiment of the present invention.

Next, the incidental information forming part 20 will be described with reference to FIG. 4. FIG. 4 is a schematic view showing an incidental information display screen 200 of the ultrasonic apparatus 1 in the embodiment of the invention. The incidental information forming part 20 (corresponds to an example of a portion of the "image generator" in the present invention) receives incidental information for each item, and generates the incidental display screen 200 in a state where the incidental information display screen 200 having not been generated yet is displayed by the display 90.

The incidental information forming part 20 receives the incidental information having been classified and transmitted by the incidental information acquiring part 10, separately for identification information, patient information and examination information, and also receives the information for each item, such as patient ID, health status of the subject and the name of the doctor requesting the examination.

Moreover, the incidental information forming part 20 generates incidental information image data in the following manner. The incidental information image data is for displaying the incidental information display screen 200 exemplified in FIG. 4, and is generated based on the incidental information having been separated by item and received from the incidental information acquiring part 10.

First, the controller 2 reads out screen data associated with a background image, frame and so on of the incidental information display screen 200 from the storage 70, etc. Based on the screen data, the controller 2 controls the display 90 to previously display a background image and frame of the incidental information display screen 200. The incidental information forming part 20 assigns the received incidental information to the screen data having been read out. The incidental information forming part 20 assigns the incidental information to the screen data in an arrangement and alignment having been set for each of the identification information, the patient information and the examination information, and assigns the respective information by item (patient ID, health status of the subject, name of the doctor requesting the examination, etc.). The following is a specific example of the process.

The incidental information forming part 20 processes to display previously set identification information for identification of each examination (for example, information on examination date, name of the hospital, name of the diagnosis and treatment department, etc.) in an identification information display region 201 of the incidental information display screen 200 as shown in FIG. 4. That is, the incidental information forming part 20 assigns the identification information to incidental information image data corresponding to the identification information display region 201.

Further, the incidental information forming part 20 processes so that information on opinions and additional explanations regarding patient ID, patient name, date of birth, age, gender, ethnicity, etc. as well as the patient's health status are displayed as previously set information for identification of a patient and as patient information showing the state of the body and health of the patient, in a patient information display region 202 of the incidental information display screen 200 as shown in FIG. 4. That is, the incidental information forming part 20 assigns the patient information to incidental information image data corresponding to the patient information display region 202.

Further, the incidental information forming part 20 processes so that information on the approval number of the examination, the name of the examiner, the name of the doctor requesting the examination, etc. are displayed as previously set examination information on examination, in an examination information display region 203 of the incidental information display screen 200. That is, the incidental information forming part 20 assigns the examination information to the examination information display region 203.

Thus, incidental information for each item of the identification information, the patient information and the examination information is assigned in association with each of the identification information display region 201, the patient information display region 202 and the examination information display region 203, and incidental information image data corresponding to the incidental information display screen 200 as shown in FIG. 4 is generated.

Further, the incidental information forming part 20, while displaying the incomplete incidental information display screen 200 in the display 90, sequentially assigns the incidental information to the aforementioned screen data, and transmits the incidental information image data through the generation process thereof. The display 90 receives the incidental information image data corresponding to the generation process thereof. The display 90 reflects the received data, and displays the incidental information display screen 200 corresponding to the generation process. The examiner can check the incidental information for each item while viewing the incidental information display screen 200 displayed in the display 90.

When the generation of the incidental information image data related to the incidental information display screen 200 is completed by the incidental information forming part 20, the incidental information image data is transmitted to the information processor 60. The transmission is conducted after the incidental information display screen 200 is checked by the examiner. For example, upon completion of the generation of the incidental information display screen 200, the examiner performs an operation of completing the check of the displayed incidental information via an operation part (not illustrated). Through this operation, the controller 2 receives a signal indicating the completion. The controller 2 transmits the generated incidental information image data to the information processor 60, based on the reception of the signal.

The incidental information forming part 20 may be configured so that the controller 2 determines for each of the items whether the collection of the incidental information image data has been completed, and the controller 2 transmits the generated incidental information image data to the information processor 60 based on determination that the collection of the incidental information image data has been completed for all of the items of the incidental information image data.

Further, in the present embodiment, after the completed incidental information image data is transmitted to the information processor 60, the ultrasonic imaging part 3 and the ultrasonic probe 40 (described later) operate.

(Configuration of Ultrasonic Imaging Part)

Figure 5:
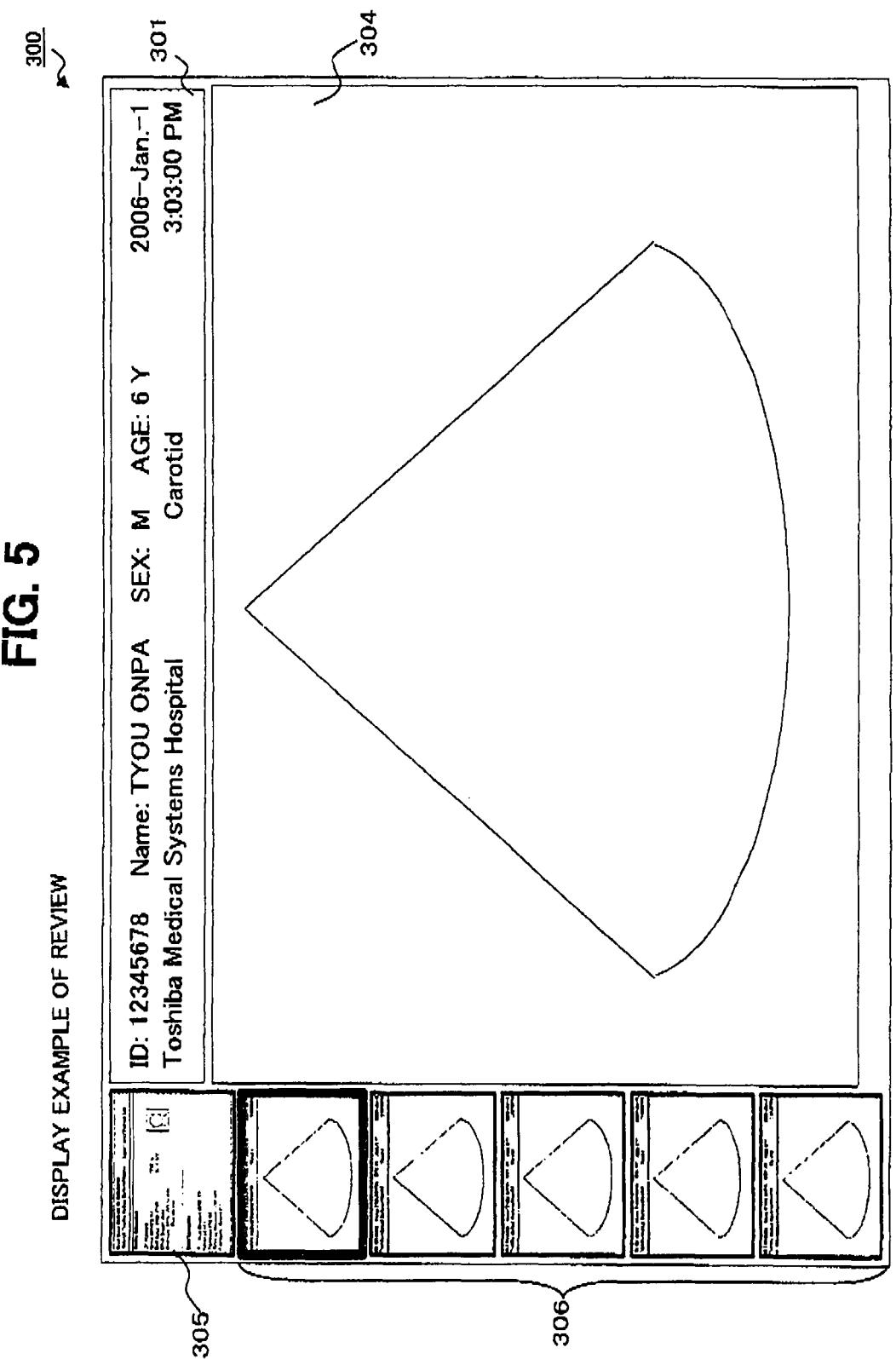
FIG. 5 is a schematic view showing an ultrasonic image display screen in the ultrasonic diagnostic apparatus in the embodiment of the present invention.

Next, the ultrasonic imaging part 3 and the ultrasonic probe 40 will be described with reference to FIGS. 3 and 5. FIG. 5 is a schematic view showing an ultrasonic image display screen 300 in the ultrasonic apparatus 1 of the embodiment of the present invention.

As shown in FIG. 3, the ultrasonic imaging part 3 (equivalent to an example of a portion of the "image generator" in the present invention) comprises a transmission/reception unit 30 and an image forming part 50. In conjunction with the reception of the incidental information image data by the information processor 60, the ultrasonic imaging part 3 starts to operation, whereby an examination starts. In the ultrasonic imaging part 3, through the examination of a subject with the ultrasonic probe 40 by the examiner, the ultrasonic image data used for displaying ultrasonic images is formed. That is, the ultrasonic imaging part 3 converts received waves reflected by the subject into a signal. Furthermore, based on the signal, the ultrasonic imaging part 3 generates ultrasonic image data indicating the inside state of the subject body.

In the ultrasonic imaging part 3, firstly, a rate pulse with a delay time is supplied to a pulsar of the transmission/reception unit 30. The pulsar of the transmission/reception unit 30 transmits a drive signal to an ultrasonic transducer of the ultrasonic probe 40 based on the rate pulse. Upon receiving the drive signal, the ultrasonic transducer converts the signal into an ultrasonic pulse, and transmits the ultrasonic pulse to a site to examine of a subject (patient). Furthermore, the ultrasonic transducer receives reflection waves from the inside tissue of the subject of the transmitted ultrasonic pulse, converts the reflection waves into an electric signal, and transmits the electric signal to the transmission/reception unit 30.

The transmission/reception unit 30 receives the electric signal of the reflection waves from the ultrasonic transducer of the ultrasonic probe 40. Furthermore, the transmission/reception unit 30 converts the electric signal into a digital signal, provides the signal with a delay time after conversion, and conducts phasing to add. The digital signal is then transmitted to the image forming part 50.

The image forming part 50 subjects the received signal from the transmission/reception unit 30 to signal processing (B-mode processing, Doppler processing, etc.). For example, the transmission/reception unit 30 performs a DSC (digital scan conversion) process to the received signal, thereby converting into an image signal string. Furthermore, by subjecting volume data to volume rendering, the transmission/reception unit 30 generates three-dimensional inside information. Or, by subjecting the received signal to an MPR (Multi Planar Reconstruction) process, the transmission/reception unit 30 generates inside information of any cross-section (MPR image data).

The inside information is assigned to the screen data. That is, among the data for displaying an ultrasonic image display region 304 shown in FIG. 5, the image forming part 50 reads out screen data for displaying the background image, frame, etc. from the storage 70. The image forming part 50 sequentially assigns collected inside information to the screen data having been read out, and generates an ultrasonic image for each frame.

Thus, the image forming part 50 generates ultrasonic image data relating to the ultrasonic image of each frame. The ultrasonic image data is data of each frame shown in the ultrasonic image display region 304 as shown in FIG. 5. The image forming part 50 transmits the generated ultrasonic image data to the information processor 60 in chronological order.

In the ultrasonic apparatus 1, based on the acquired inside information, the image forming part 50 generates an ultrasonic image. Moreover, the ultrasonic apparatus 1 diachronically and continuously displays the generated ultrasonic image for each frame in the display 90. Thus, the ultrasonic images are displayed in real time. In addition, in the ultrasonic apparatus 1 of the present embodiment, while viewing a moving image of the ultrasonic image displayed in real time, the examiner can make the moving image still displayed by using an operation part. Furthermore, by performing the operation of storing the still-displayed ultrasonic image by using an operation part, the examiner can cause the controller 2 to store the ultrasonic image in the storage 70 or the like.

The ultrasonic apparatus 1 in the present embodiment is capable of performing not only the process of transmitting all the ultrasonic images on the frame basis to the information processor 60 but also a process as described below. That is, the controller 2 of the ultrasonic apparatus 1 is also capable of transmitting only a still image of the stored ultrasonic image selected and stored by the examiner, to the information processor 60.

(Configuration of Information Processor)

Next, the configuration of the information processor 60 will be described with reference to FIGS. 3 to 5.

In conjunction with an operation of completing the check by the examiner, the information processor 60 (equivalent to an example of the "information processor" in the present invention) firstly receives incidental information image data from the incidental information forming part 20. When receiving the incidental information image data, the information processor 60 processes to form the incidental information display screen 200 shown in FIG. 4 in an independent frame from that of an ultrasonic image. Furthermore, the information processor 60 conducts information processing of the incidental information image data so as to form the incidental information image data as a series of images with the ultrasonic image. Moreover, the information processor 60 temporarily stores the generated incidental information display screen 200 in order to generate the ultrasonic image display screen 300 shown in FIG. 5.

By configuring to temporarily store the incidental information display screen 200 in accordance with the operation of check completion by the examiner, it is possible to temporarily store the incidental information display screen 200, as part of the work of checking incidental information such as the identification information, the patient information and the examination information. Moreover, the examiner does not need to perform any special operation. Therefore, it is possible to prevent occurrence of a problem such as forget to record the incidental information. Furthermore, it becomes possible to conduct storing operations for the incidental information display screen 200 without troubling the examiner.

Next, when sequentially receiving the ultrasonic image data from the image forming part 50, the information processor 60 temporarily stores the data in the reception chronological order.

The information processor 60 receives an instruction indicating the completion of collecting inside information of a subject and the completion of generating ultrasonic image data. Upon receiving the completion instruction, the information processor 60 conducts information processing so as to display the ultrasonic image data of each frame displayed in the ultrasonic image display region 304 and the incidental information image data relating to the aforementioned incidental information display screen 200, which have been temporarily stored, as images independent from each other. Furthermore, the information processor 60 conducts information processing for forming the incidental information image data as a series of images with the ultrasonic image. Here, the information processor 60 recognizes completion of generation of the ultrasonic image data (completion of collection of the inside information) of the subject when, for example, the examiner performs an operation of examination completion by using an operation part (not illustrated).

Further, the information processor 60 conducts information processing so that the incidental information display screen 200 and the ultrasonic images are displayed in the generation order. In this case, in the present embodiment, the information processor 60 conducts information processing so that the incidental information display screen 200 is displayed first and then the ultrasonic images are displayed in the chronological order. This is because, among a series of images in one examination, the incidental information image data relating to the incidental information display screen 200 is generated first.

Further, after the information processing of the incidental information image data and the ultrasonic image data, the information processor 60 reads out screen data for displaying the background image, frames, etc. from the storage 70, among data for displaying the ultrasonic image display screen 300. After reading out the screen data, the information processor 60 assigns the image data having been subjected to the information processing, to the screen data, and generates review image data. The review image data is used for displaying the ultrasonic image display screen 300 (review screen). The review image data is generated as described below, for example.

The information processor 60 conducts information processing so that a reduced image (thumbnail) of the incidental information display screen 200 and a reduced image of the ultrasonic image are displayed in a reduced incidental-information image 305 or a reduced ultrasonic image 306 as shown in FIG. 5 are displayed.

Furthermore, the information processor 60 conducts information processing so that an ultrasonic image corresponding to the selected reduced image (305 or 306) or the incidental information display screen 200 is displayed in the ultrasonic image display region 304. Thus, review image data used for displaying the ultrasonic image display screen 300 shown in FIG. 5 is generated.

Further, after completion of generation of the review image data for the examination, the information processor 60 stores the review image data into the storage 70, or outputs the data to the printer 80 or the display 90. In addition, the information processor 60 may output the review image data to a server 100 such as a PACS (Picture Archiving and Communication System).

Thus, the information processor 60 of the ultrasonic apparatus 1 in the present embodiment processes to display (or print) the incidental information display screen 200 prior to the ultrasonic image. Therefore, an image interpreter of the ultrasonic image in the examination can conduct image interpretation or diagnoses after checking the incidental information such as the identification information, patient information, examination information, etc. As a result, it becomes possible to contribute to the enhancement of diagnostic accuracy.

Further, by executing information processing to form an image of the incidental information such as the identification information, the patient information and the examination information, so as to become a series of images with the ultrasonic images and independent from the ultrasonic images (incidental information display screen 200), it becomes possible to store, display and print the incidental information as an image. Consequently, even if there is a difference in network standards (DICOM etc.) of the medical image management systems between a medical image processing device and a viewer, it becomes possible to easily view detailed incidental information regarding the examination such as examination information and patient information. Moreover, even if the DICOM information is added to the ultrasonic image in the medical image management system but the viewer has no function for utilizing the DICOM information, it becomes possible to easily view detailed incidental information regarding the examination such as examination information and patient information. Moreover, because the incidental information is imaged as incidental information display screen 200, there is no need to install any special function in the display device, for viewing the detailed incidental information in the examination.

In addition, by taking in the incidental information into the ultrasonic image display screen 300 as one image and generating the screen, the problem of display space for the incidental information does not occur. As a result, the incidental information display screen 200 makes it possible to display more details of the identification information, the patient information and the examination information in more details of identification information, patient information, and examination information.

(Operation)

Figure 6:
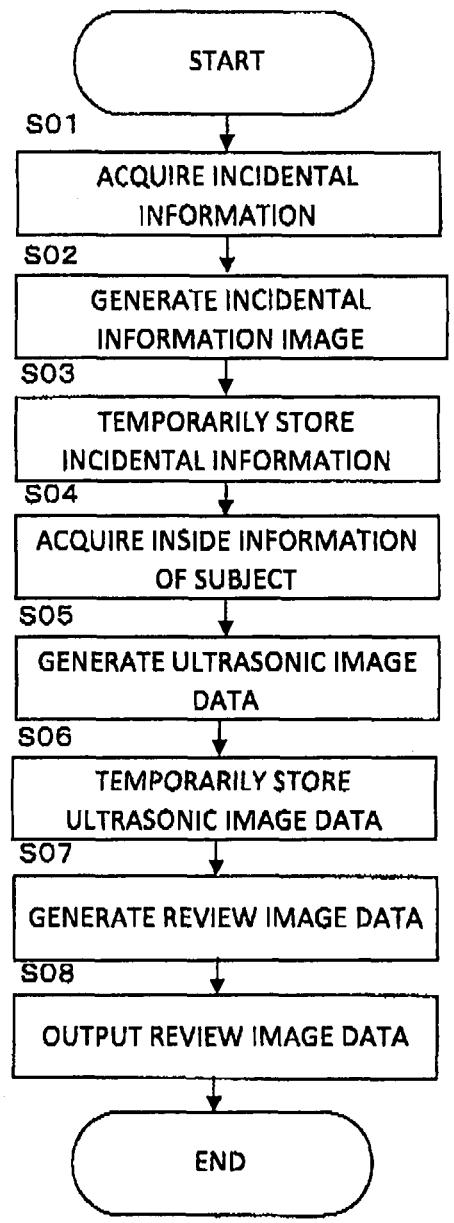
FIG. 6 is a flowchart for explaining a series of operations in an examination using the ultrasonic diagnostic apparatus in a first embodiment of the present invention.

An operation of the aforementioned ultrasonic diagnostic apparatus 1 of this embodiment will be described with reference to FIG. 6. FIG. 6 is a flowchart for explaining a series of operations of the ultrasonic apparatus 1 in the first embodiment of the present invention.

(Step 1)

The incidental information acquiring part 10 receives order information that the ultrasonic apparatus 1 has received from the HIS or RIS, information previously inputted by an examiner, or information such as an electronic medical record previously stored in the storage 70 or the like. The incidental information acquiring part 10 acquires incidental information such as identification information, examination information and patient information, based on the acquired order information or the like. Furthermore, the incidental information acquiring part 10 classifies the acquired incidental information in items, and transmits the classified information to the incidental information forming part 20.

(Step 2)

The incidental information forming part 20 receives the incidental information transmitted from the incidental information acquiring part 10 by item, and also reads out screen data from the storage 70. Further, the incidental information forming part 20 assigns the incidental information classified in the items to the screen data having been read out, for each of the identification information, the patient information and the examination information. Thus, the incidental information forming part 20 forms incidental information image data. For example, when the examiner conducts an operation of finishing check of the incidental information by using an input part (not illustrated), the incidental information forming part 20 finishes generation of the incidental information display screen 200, based on the operation. The incidental information image data having been formed is transmitted to the information processor 60.

(Step 3)

The information processor 60 executes information processing of the incidental information image data relating to the incidental information display screen 200 transmitted from the incidental information forming part 20, as an independent image from ultrasonic images. Furthermore, the incidental information forming part 20 executes information processing of the incidental information image data, as a series of images with the ultrasonic images. The incidental information forming part 20 temporarily stores the incidental information image data after the information processing of the incidental information image data.

(Step 4)

The controller 2 starts the operation of the ultrasonic imaging part 3 in conjunction with temporary storage of the incidental information image data. The examiner starts scan by the ultrasonic probe 40, and the controller 2 starts collecting inside information of a subject via the ultrasonic probe 40 by the ultrasonic imaging part 3.

(Step 5)

When the inside information of the subject is collected by the ultrasonic probe 40, a signal regarding the inside information of the subject is transmitted to the transmission/reception unit 30 of the ultrasonic imaging part 3 from the ultrasonic probe 40. The transmission/reception unit 30 transmits a signal obtained by converting a reflection wave of an ultrasonic pulse from the subject, to the image forming part 50. Upon receiving the signal, the image forming part 50 conducts signal processing and image processing. Moreover, the image forming part 50 reads out the screen data from the storage 70, and generates ultrasonic image data based on the screen data and the inside information of the subject having been subjected to the image processing. The image forming part 50 transmits the generated ultrasonic image data of each frame to the information processor 60 in chronological order.

(Step 6)

The information processor 60 receives the ultrasonic image data of each frame from the image forming part 50. The information processor 60 temporarily stores the received ultrasonic image data in chronological order.

(Step 7)

After the examiner performs the operations of examination completion, the information processor 60 executes information processing of the incidental information image data regarding the incidental information display screen 200 and the ultrasonic image data regarding the ultrasonic images, which have been temporarily stored, so as to be displayed in the generation order. The information processor 60 then generates review image data regarding the ultrasonic image display screen 300.

(Step 8)

After finishing generation of the review image data, the information processor 60 outputs the review image data to at least one of the following: the storage 70, the printer 80, the display 90, or the server 100. The output destination is designated arbitrarily by the examiner.

Figure 7:
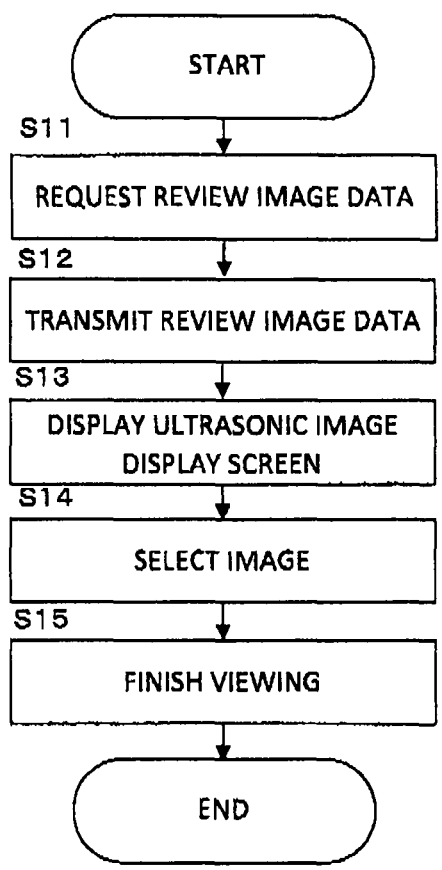
FIG. 7 is a flowchart for explaining a series of operations when viewing the ultrasonic image display screen having been subjected to information processing by the ultrasonic diagnostic apparatus in the first embodiment of the present invention.

Next, an example of a series of operations in the event of viewing the ultrasonic image display screen 300 generated by the aforementioned ultrasonic diagnostic apparatus 1 of this embodiment will be described with reference to FIG. 7. FIG. 7 is a flowchart for explaining the series of operations in the event of viewing the ultrasonic image display screen 300 for which information processing has been conducted using the ultrasonic apparatus 1 of the first embodiment in the present invention.

(Step 11)

A person viewing the images designates one examination from the examination list screen based on identification information, by using an operation part (not illustrated), etc. of an image display device 110. When the viewing person designates one examination, the image display device 110 is requested to display the ultrasonic image display screen 300 regarding the designated examination. In response to the request, the image display device 110 requests the server 100 for review image data regarding the ultrasonic image display screen 300.

(Step 12)

Upon receiving the request for the data regarding the ultrasonic image display screen 300, the server 100 transmits review image data responsive to the request selected from among the stored review image data, to the image display device 110.

(Step 13)

The image display device 110 displays the ultrasonic image display screen 300 regarding the review image data, in response to reception of the review image data having been requested to the server 100. At this moment, the image display device 110 displays a series of images, i.e., reduced images of the incidental information display screen 200 and the ultrasonic images (see FIG. 5, reference numbers 305 and 306), on the ultrasonic image display screen 300. Furthermore, the image display device 110 displays part of the identification information in the identification information display region 301. Moreover, the image display device 110 displays either the incidental information display screen 200 or the ultrasonic image of a frame having been selected, in the ultrasonic image display region 304. In this embodiment, information processing is conducted so that the images are displayed in the generation order. Therefore, at the initial moment when the ultrasonic image display screen 300 is displayed, the incidental information display screen 200 is displayed in the ultrasonic image display region 304. The viewing person can check detailed incidental information (examination information, patient information, etc.) necessary for diagnosis etc. by viewing the incidental information display screen 200 at the initial moment when the ultrasonic image display screen 300 is displayed.

(Step 14)

The viewing person can select either the reduced incidental-information image 305 or the reduced ultrasonic image 306 as shown in FIG. 5 by using the operation part in the image display device 110. Through this selection, an image responsive to the selection is displayed in the ultrasonic image display region 304. That is, if the reduced incidental-information image 305 is selected, the incidental information display screen 200 is displayed in the ultrasonic image display region 304, and if the reduced ultrasonic image 306 is selected, an ultrasonic image of each frame responsive to the selection is displayed in the ultrasonic image display region 304.

(Step 15)

In the process of viewing an ultrasonic image, the viewing person can select the reduced incidental-information image 305 again from among the reduced images (305, 306) in order to check the incidental information again. As described, in a case where the viewing person has operated to select the reduced incidental-information image 305 again, the image display device 110 displays the incidental information display screen 200 in the ultrasonic image display region 304. In a case where the viewing person conducts a selection operation to display other ultrasonic images, an ultrasonic image responsive to the selection is displayed. As described, the display for viewing is performed. When the diagnosis or the like ends, the display ends through an ending operation, etc. by the operator, (Actions and Advantageous Effects)

The actions and effects of the ultrasonic apparatus 1 in this embodiment as described above will be described.

The ultrasonic apparatus 1 in this embodiment generates, in the incidental information forming part 20, incidental information image data including the details of identification information, patient information and examination information that are used for display of the incidental information display screen 200. Further, the ultrasonic apparatus 1 generates, in the information processor 60, the incidental information display screen 200 based on the incidental information image data. Further, the information processor 60 executes information processing of the incidental information display screen 200 to be displayed in series with ultrasonic images. Moreover, the information processor 60 is configured to generate review image data associated with the ultrasonic image display screen 300.

Thus, regarding incidental information, ultrasonic images and incidental information image data are displayed independently from each other and also as a series of images, so that a problem of limitation of a display space does not occur, and it is possible to display more details of identification information, patient information, examination information, etc. Thus, it becomes possible to contribute to increase of the accuracy of diagnosis or the like.

In addition, the incidental information display screen 200 is not displayed in association with part of ultrasonic images, but is displayed as an independent image from ultrasonic images. Furthermore, the incidental information display screen 200 is displayed as a series of images with ultrasonic images. Therefore, a person viewing the ultrasonic image display screen 300 can check information necessary for diagnosis or the like through a simple operation at the time of viewing. Moreover, when checking the necessary information, the viewing person does not need to perform any special operation such as data analysis of the ultrasonic image display screen 300 and separate preparation of electronic medical records. Besides, it is not required to install a special function in the image display device 110 or the like for the viewing person to view incidental information. As a result, it is possible to increase the efficiency in diagnosis etc.

In addition, in some cases, there are differences in network standard (DICOM, etc.) of management systems of medical images between a medical image processing device and a display device such as a viewer. Moreover, in a case where DICOM information is added to an ultrasonic image in the medical image management system, there may be a case where the viewer has no function for utilizing the DICOM information. Even in such cases, regardless of the differences in standard, the ultrasonic apparatus 1 in this embodiment makes it possible to easily view detailed incidental information on examination such as examination information and patient information, as a series of images.

Furthermore, the ultrasonic apparatus 1 in this embodiment executes information processing in a generation order of images. The ultrasonic apparatus 1 is configured to display the incidental information display screen 200 and the ultrasonic images in the generation order.

Therefore, the apparatus is configured to, when the ultrasonic image display screen 300 is displayed in the image display device 110 or the like, firstly cause a person viewing the screen to view the incidental information display screen 200. That is, the apparatus is capable of, before the viewing person starts viewing ultrasonic images, causing the viewing person to check the details of examination information and patient information. As a result, it becomes possible to contribute to increase of the accuracy of diagnosis or the like.

Further, a person viewing ultrasonic images may continuously interpret ultrasonic images associated with a plurality of subjects in the case of, for example, a group examination. Even in such a case, if the stored ultrasonic images are from the ultrasonic apparatus 1 of this embodiment, the incidental information display screen 200 is displayed between the ultrasonic images that are continuously displayed. Therefore, the viewing person can check the incidental information display screen 200, thereby recognizing that the subject related to the continuously displayed ultrasonic images has switched.

In addition, the ultrasonic apparatus 1 in this embodiment is configured to temporarily store the incidental information display screen 200 having been subjected to information processing by the information processor 60, in accordance with an operation of check completion of incidental information by the examiner.

Thus, the examiner can temporarily store the incidental information display screen 200 as a part of a checking work of incidental information such as identification information, patient information and examination information without any special operation. Accordingly, it is possible to prevent a situation of forgetting to record incidental information or the like from arising. Furthermore, it becomes possible to conduct storing operations of the incidental information display screen 200 without troubling the examiner.

SECOND EMBODIMENT

Next, the ultrasonic apparatus 1 in a second embodiment of the present invention will be described.
(Configuration)

The ultrasonic diagnostic apparatus in the second embodiment is different from the ultrasonic apparatus 1 in the first embodiment described before, in operations of the incidental information forming part 20 and information processor 60, and is identical to the ultrasonic apparatus 1 in the first embodiment, in other parts. Below, the operations different from the ultrasonic apparatus 1 in the first embodiment will be described.

In the ultrasonic apparatus 1 in the second embodiment, the examiner is able to select incidental information displayed in the incidental information display screen 200, for each item of the incidental information. That is, the incidental information forming part 20 of the second embodiment reflects only the incidental information of the selected item among the incidental information acquired by the incidental information acquiring part 10, on the incidental information image data, and generates the incidental information display screen 200. The selection of the incidental information for each item by the examiner is executed in the following manner, for example.

Screen data used for the selection of incidental information for each item is prestored in the storage 70. The controller 2 reads out the screen data used for the selection of incidental information, and causes the display 90 to display the data. Next, by using an operation part or the like, the examiner selects incidental information to display in the incidental information display screen 200, on the displayed incidental information selection screen. When the examiner performs the selection, the incidental information forming part 20 forms only incidental information associated with the item responsive to the selection, as incidental information image data, from among incidental information received from the incidental information acquiring part 10. The selection of the item of incidental information by the examiner is conducted by filling in a checkbox on the selection screen displayed in the display 90, for example.

Furthermore, in the ultrasonic apparatus 1 of the present embodiment, the examiner or others is able to set a layout in the incidental information display screen 200. The layout formats the disposition and the arrangement of identification information, patient information, and examination information, etc. for each item in the incidental information display screen 200. The incidental information forming part 20 generates incidental information image data to display the incidental information display screen 200 based on the layout setting. The selection of incidental information by each item by the examiner is, for example, conducted as follows.

Screen data to be used for the layout setting of the incidental information display screen 200 is prestored in the storage 70. The controller 2 reads out screen data for the layout setting and displays a screen to be used for the layout setting in the display 90. Furthermore, the display is configured to be displayed before or after the selection in the previously described selection screen of incidental information. Next, the examiner sets the layout of the incidental information display screen 200 on the layout setting screen by an operation part or the like. As for the setting method, it is also possible to configure so that any one of a plurality of preliminarily stored layouts can be selected by the examiner through an operation part or the like. As for other examples of setting methods, it is also possible to form a configuration in which the arrangement and the disposition of each item is determined by the examiner by dragging through the display region of identification information, patient information, and examination information, etc. with an operation part such as a mouse or the like.

By configuring the incidental information forming part 20 and the information processor 60 as described, it becomes possible to display incidental information according to the needs of the viewing person. As a result, contributions to enhancing the efficiency and accuracy of diagnosis, etc, become possible.

Furthermore, the information processor 60 in the second embodiment does not complete the generation of the incidental information display screen 200 even when the collection of inside information of a subject begins. Moreover, the information processor 60 in the present embodiment is configured so that the incidental information acquiring part 10 acquires comments and opinions input by the examiner during the collection operation as incidental information. The comments may be opinions from an examiner or an assistant of the examiner, additional explanations, and the like.

For example, once the examiner inputs comments or opinions related to the examination by an inputting means or by voice input during an examination, the incidental information acquiring part 10 acquires the comments and the opinions as incidental information. The incidental information acquiring part 10 transmits the acquired incidental information to the incidental information forming part 20.

Upon receiving the incidental information as comments and opinions, the incidental information forming part 20 first reads out temporarily stored incidental information image data. In addition, the incidental information forming part 20 again generates incidental information image data again by incorporating the received incidental information into the incidental information image data. As described, the incidental information forming part 20 incorporates the comments and opinions into the incidental information display screen 200 associated with the examination. Furthermore, after the generation of ultrasonic images is finished, the incidental information forming part 20 transmits the incidental information image data, to which comments or opinions, etc. have been incorporated, to the information processor 60.

After receiving the incidental information image data, to which comments or opinions, etc. have been incorporated, the information processor 60 conducts information processing of the incidental information image data and ultrasonic image data. As a result, the information processor 60 generates review image data associated with the ultrasonic image display screen 300.

With the described configuration, incidental information such as comments or opinions, etc. of the examiner may be incorporated and displayed in the incidental information display screen 200. As a result, because the viewing person is able to view and confirm the incidental information, it becomes possible to further enhance the accuracy and efficiency of diagnosis or the like.

(Operation)

Figure 8:
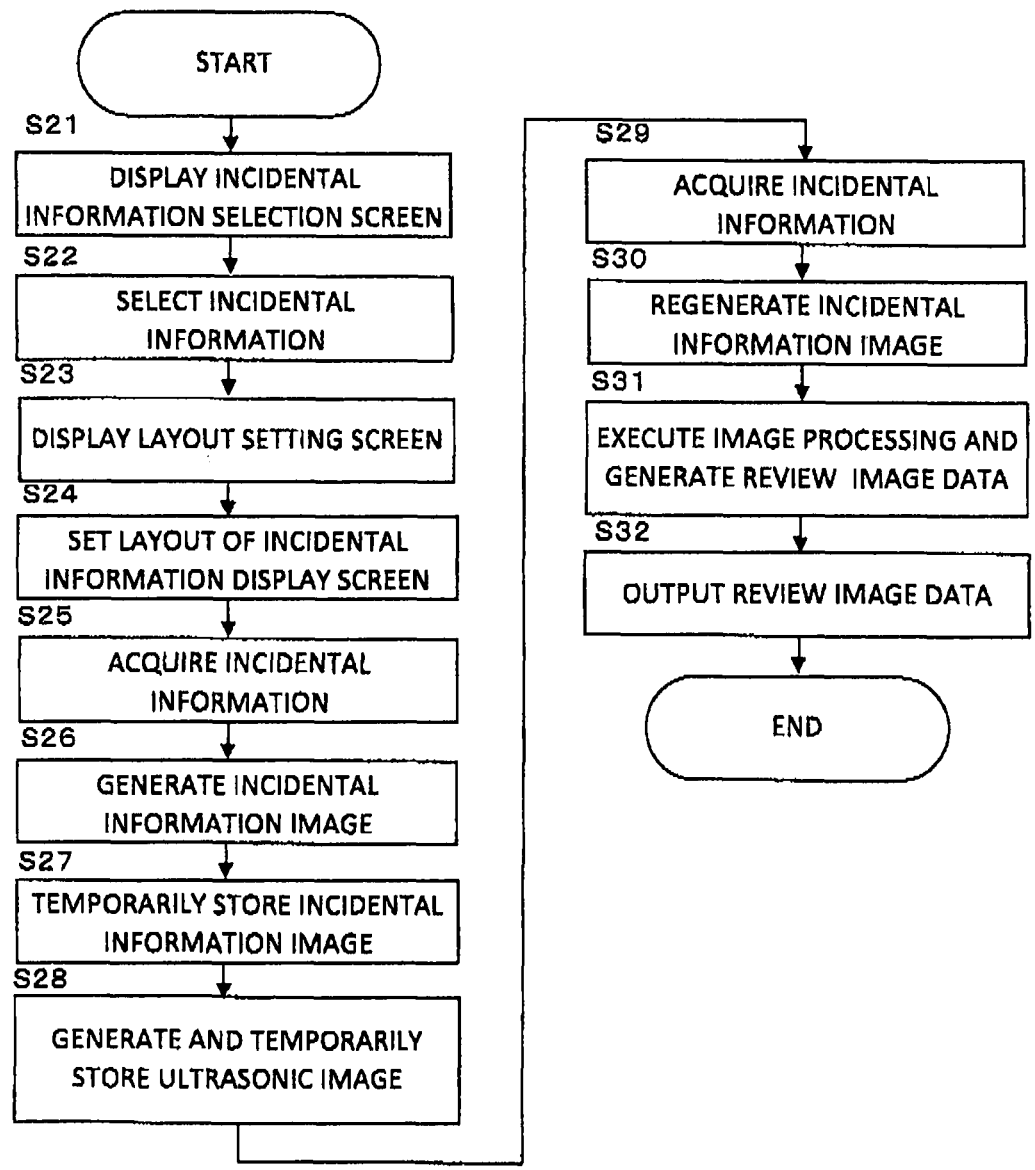
FIG. 8 is a flowchart for explaining a series of operations in an examination using the ultrasonic diagnostic apparatus in the second embodiment of the present invention.

Operations of such ultrasonic diagnostic apparatus 1 in the present embodiment will be described with reference to FIG. 8. FIG. 8 is a flowchart for explaining a series of operations in an examination using the ultrasonic apparatus 1 of the second embodiment.

(Step 21)

The controller 2 reads out, from the storage 70 or the like, screen data of a screen that is used for the selection of items of incidental information to be displayed on the incidental information display screen 200, and displays the screen in the display 90.

(Step 22)

As a result of the selection of the items of incidental information to be displayed in the incidental information display screen 200 according to the selection by the operator, incidental information to be imaged as incidental information image data is set.

(Step 23)

When the incidental information is set, the controller 2 reads out screen data used for setting the layout of the incidental information in the incidental information display screen 200, from the storage 70 or the like. Furthermore, the controller 2 displays the screen based on the screen data in the display 90.

(Step 24)

The layout for each item of the incidental information to be displayed on the incidental information display screen 200 is set according to the settings of the operator.

(Step 25)

The incidental information acquiring part 10 acquires order information received by the ultrasonic apparatus 1 from the HIS/RIS, information entered in advance by an examiner, information such as electronic medical records, etc. preliminarily stored in the storage 70, or the like. The incidental information acquiring part 10 acquires incidental information such as identification information, examination information, and patient information based on the acquired order information. Furthermore, the incidental information acquiring part 10 can, for example, receive a signal indicating that the collection of the incidental information has been completed through an operation by the examiner. Upon receiving the signal, the incidental information acquiring part 10 classifies the acquired incidental information for each item and transmits the same to the incidental information forming part 20.

(Step 26)

Once the incidental information transmitted from the incidental information acquiring part 10 is received for each item, the incidental information forming part 20 reads out screen data from the storage 70. The incidental information forming part 20 configures incidental information image data by assigning the incidental information of each item to the screen data that has been read out. When the incidental information forming part 20 assigns the incidental information, the incidental information forming part 20 assigns only the items of the incidental information that have been selected and set in Step 21 and 22 to the screen data. Furthermore, the incidental information forming part 20 is assigned to the screen data by identification information, patient information, and examination information in the layout that has been set in Step 24. Moreover, the incidental information forming part 20 transmits the incidental information image data to the information processor 60.

(Step 27)

After the examiner confirms the incidental information with reference to the screen, an operation may be conducted in the ultrasonic apparatus 1 to the effect that the confirmation of the incidental information has been completed. With this operation, the information processor 60 temporarily stores the incidental information image data associated with the incidental information display screen 200, which has been received from the incidental information forming part 20.

(Step 28)

In conjunction with the temporarily storing of the incidental information image data, the controller 2 starts operations of the ultrasonic imaging part 3. Then, scanning by the ultrasonic probe 40 becomes possible. Once the ultrasonic probe 40 starts the operations, the examiner starts collecting inside information of a subject via the ultrasonic probe 40. Once the inside information of the subject is collected, the image forming part 50 reads out screen data from the storage 70. Furthermore, the image forming part 50 generates the screen data and ultrasonic image data from the inside information of the subject that was subjected to image processing. Moreover, the image forming part 50 transmits the generated ultrasonic image data to the information processor 60 in chronological order. Once the ultrasonic image data of each frame is received from the image forming part 50, the information processor 60 temporarily stores the ultrasonic image data in the received order.

(Step 29)

The examiner is able to input comments or opinions regarding the examination during the collection of the inside information of the subject. Once the comments or opinions are input by the examiner, the incidental information acquiring part 10 acquires the comments and the opinions as incidental information and transmits the same to the incidental information forming part 20.

(Step 30)

Upon receiving the incidental information such as comments, etc. input during an examination, the incidental information forming part 20 regenerates incidental information image data again. However, according to the layout settings conducted by the examiner, if the incidental information such as the comments or the like is not included in the items of the selected and set incidental information, the regeneration of the incidental information image data is not conducted.

(Step 31)

Through an operation of examination completion by the examiner, the incidental information forming part 20 transmits the incidental information image data, to which comments and opinions, etc. have been incorporated, to the information processor 60. Once the incidental information image data is received, the information processor 60 conducts information processing to display the incidental information image data and the temporarily stored ultrasonic image data in the generated order. Furthermore, the incidental information forming part 20 generates review image data associated with the ultrasonic image display screen 300.

(Step 32)

Once the generation of the ultrasonic image display screen 300 has been completed, the information processor 60 outputs the data associated with the ultrasonic image display screen 300 to the storage 70, printer 80, display 90, or server 100.

(Modification)

Next, a modification of the ultrasonic diagnostic apparatus of the present invention will be described.

Although the above first embodiment and second embodiment describe examples in which the present invention is applied to ultrasonic diagnostic apparatus, the present invention is not limited to these configurations and can be applied to various devices with modalities for medical image diagnosis, including X-ray diagnostic apparatuses, X-ray CT devices, MRI devices, ultrasonic diagnostic apparatus, NM devices, or the like.

Furthermore, in the above first embodiment and second embodiment, although the controller 2 is configured to store still images of ultrasonic images, the present invention is not limited to this. That is, as for the image forming part 50, it is possible to configure a moving image by diachronically and continuously storing generated ultrasonic images of each frame. In this modification, information processing is conducted by the information processor 60 to display the incidental information screen 200 before the first frame of the moving image. Also, in this modification, before the viewing person who has viewed the stored moving image of ultrasonic images starts viewing the moving image, it is possible to allow the viewing person to confirm the details of examination information and patient information. As a result, it becomes possible to contribute to enhancing the accuracy of diagnosis or the like.

Moving images are stored in a moving picture file format for general purposes. For example, the following file formats can be used: AVI (Audio Video Interleave), ASF (Advanced Systems Format), FLV (Flash Video), OGM (Ogg Media), OGG (Ogg file), MPEG (Moving Picture Experts Group), MOV (QuickTime Movie), RealVideo, VG2, DivX (DivX Media Format), etc.

What is claimed is:

1. A medical image processing apparatus comprising:
    an image generator configured to generate a plurality of inside images based on inside information showing a tissue within a subject acquired in an examination of the subject and to generate an incidental information image which is formed per frame, upon receiving incidental information including at least either information on the subject or information on the examination, based on the incidental information, and to generate a reduced incidental information image and a plurality of reduced inside images; and
    an information processor configured to arrange the reduced incidental image and the plurality of reduced inside images in a first display area and, in response to a selection by an operator of one of the reduced images, to display a corresponding inside image or incidental image in a same second display area.

2. The medical image processing apparatus according to claim 1, wherein:
    the information processor executes the information processing of the incidental information image upon receiving an instruction of check completion of the incidental information.

3. The medical image processing apparatus according to claim 1, wherein:
    the image generator generates the plurality of inside images after the incidental information image is generated based on the incidental information; and
    the information processor executes the information processing so that the incidental information image comes before the plurality of inside images in an arrangement order of images per frame.

4. The medical image processing apparatus according to claim 3, wherein:
    during or after acquisition of the inside information, the image generator acquires an opinion or supplemental explanation of an examiner involved in the examination as part of the incidental information, and generates the part of the incidental information as the incidental information image; and
    upon receiving an ending instruction of the examination, the information processor forms the incidental information image including the part of the incidental information in an independent frame from the inside image, and executes image processing of the incidental information image as a series of images with the inside image, and outputs the image.

5. The medical image processing apparatus according to claim 4 further comprising:
    a setting part configured to display the incidental information per item on a display, thereby making it possible to select per item the incidental information displayed in the incidental information image, and making it possible to set disposition and arrangement per item of the incidental information in the incidental information image in response to an operation by the examiner, wherein:
    the image generator generates the incidental information image in the set disposition, based on the incidental information selected by the setting part.

6. The medical image processing apparatus according to claim 1, wherein:
    the information processor executes information processing of the plurality of inside images as moving images in a general-purpose moving image file format.

7. A recording method in a medical image processing apparatus configured to generate a plurality of inside images based on inside information showing a tissue within a subject acquired in an examination of the subject, for recording incidental information related to the examination which is formed per frame, the recording method comprising:
    acquiring the incidental information related to the examination;
    generating an incidental information image based on the incidental information upon receiving the incidental information including at least either information on the subject or information on the examination, and generating a reduced incidental information image;
    collecting the inside information;
    generating the plurality of inside images based on the inside information and generating a plurality of reduced inside images;
    arranging the reduced incidental information image and the plurality of reduced inside images in a first display area and in response to a selection by an operator of one of the reduced images, displaying a corresponding inside image or incidental information image in a same second display area.

* * * * *